(12) United States Patent　　(10) Patent No.: US 8,866,087 B2
Pistorius et al.　　(45) Date of Patent: Oct. 21, 2014

(54) SYSTEMS AND METHODS FOR IMPROVING THE QUALITY OF IMAGES IN A PET SCAN

(75) Inventors: Stephen Pistorius, Winnipeg (CA); Hongyan Sun, Winnipeg (CA)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 13/977,893

(22) PCT Filed: May 29, 2012

(86) PCT No.: PCT/CA2012/050352
§ 371 (c)(1),
(2), (4) Date: Jul. 1, 2013

(87) PCT Pub. No.: WO2013/177661
PCT Pub. Date: Dec. 5, 2013

(65) Prior Publication Data
US 2014/0158890 A1　　Jun. 12, 2014

(51) Int. Cl.
*G01T 1/29* (2006.01)
*G06T 11/00* (2006.01)
*G01T 1/164* (2006.01)

(52) U.S. Cl.
CPC ............. *G01T 1/2985* (2013.01); *G06T 11/005* (2013.01); *G01T 1/1647* (2013.01)
USPC ....................... 250/363.04; 382/131; 600/436

(58) Field of Classification Search
CPC ........... G01T 1/2985; G01N 2223/108; G01R 33/481; A61N 2005/1052; G06T 2207/10104; H01J 2237/06391
USPC ........................ 250/363.03; 382/131; 600/436
See application file for complete search history.

(56) References Cited

U.S. PATENT DOCUMENTS 7,888,651 B2　　2/2011　Chinn et al.
2010/0059682 A1　3/2010　Conti

OTHER PUBLICATIONS

Sun et al. (2012). "Improvements in image quality when using patient outline constraints with a generalized scatter PET reconstruction algorithm." Nuclear Science Symposium and Medical Imaging Conference (NSS/MIC), 2012 IEEE. pp. 3083-3089.*
"A method to use tissue-scattered coincidence photons in positron emission tomography", http://flintbox.com/public/project/13252/, Feb. 1, 2012.
International Search Report and Written Opinion in PCT/CA2012/050352 mailed Feb. 11, 2013, pp. 1-7.

(Continued)

*Primary Examiner* — Casey Bryant
(74) *Attorney, Agent, or Firm* — Foley & Lardner LLP

(57) ABSTRACT

Systems, devices and methods of reconstructing an image from a positron emission tomography scan that may include detecting a plurality of photons selected from scattered photons and unscattered photons by a plurality of detectors, identifying a time interval for each of the plurality of photons by a processing device, matching each of the plurality of photons into a plurality of pairs of coincident photons based upon a substantially simultaneous time interval identified by the processing device, measuring an energy produced by each of the plurality of photons by the plurality of detectors, determining a scattering angle for each pair of coincident photons from an annihilation point relative to the position of the plurality of detectors by the processing device based on the energy produced and reconstructing an image using a reconstruction algorithm, wherein the reconstruction algorithm uses the scattering angle of each pair of coincident photons.

25 Claims, 8 Drawing Sheets

(56) References Cited

OTHER PUBLICATIONS

J. Nuyts et al., "Maximum-Likelihood Expectation-Maximization Reconstruction of Sinograms with Arbitrary Noise Distribution Using NEC-Transformations," IEEE Transactions on Medical Imaging, vol. 20, No. 5, pp. 365-375 (May 5, 2001).
L M Popescu, et al., "PET energy-based scatter estimation and image reconstruction with energy-dependent corrections", IOPscience, Physicians in Medicine and Biology, vol. 51, No. 11, p. 1-2 (2006).
Maurizio Conti, et al., "Reconstruction of scattered and unscattered PET coincidences using TOF and energy information", IOPscience, Physics in Medicine and Biology, Sep. 17, 2012, mnVol. 57, No. 15.
R. Badawi, "Introduction to PET Physics," Jan. 12, 1999.
Richard M. Leary, et al., "Statistical approaches in quantitative positron emission tomography", Statistics and Computing (2000) 10, 147-165.
Siemens medical, "Scatter Correction in 3D Positron Emission Tomography", www.siemens.com/medical, pp. 1-4 (2006).
Accorsi, R. et al., "Optimization of a fully 3D single scatter simulation algorithm for 3D PET," Physics in Medicine and Biology, vol. 49, No. 12, pp. 2577-2598 (2004).
Adam, L. E. et al., "Scatter correction using a dual energy window technique for 3D PET with NaI(Tl) detectors," IEEE Nuclear Science Symposium & Medical Imaging Conference. Toronto, Que, Can, IEEE, vol. 3, pp. 2011-2018 (1998).
Alnaaimi, M. A., et al., "Performance evaluation of a pixellated Ge Compton camera," Physics in Medicine and Biology, vol. 56, No. 12, pp. 3473-3486 (2011).
Ay, M. R. And Zaidi, H., "Assessment of errors caused by X-ray scatter and use of contrast medium when using CT-based attenuation correction in PET," European Journal of Nuclear Medicine and Molecular Imaging, vol. 33, No. 11, pp. 1301-1313 (2006).
Bai, C., et al., "A Generalized Model for the Conversion from CT Numbers to Linear Attenuation Coefficients" IEEE Transactions on Nuclear Science, vol. 50, No. 5, pp. 1510-1515 (2003).
Bailey, D. L. and Meikle, S. R. "A convolution-subtraction scatter correction method for 3D PET," Physics in Medicine and Biology, vol. 39, No. 3: pp. 411-424 (1994).
Bailey, D. L., "Quantitative procedures in 3D PET," The Theory and Practice of 3D PET, vol. 32 pp. 55-109 (1998).
Bailey, D. L., "Transmission scanning in emission tomography." European Journal of Nuclear Medicine, vol. 25, No. 7: 774-787 (1998).
Barret, O., et al., "Monte Carlo simulation and scatter correction of the GE Advance PET scanner with SimSET and Geant4," Physics in Medicine and Biology, vol. 50, No. 20, pp. 4823-4840 (2005).
Basu, S. et al., "Quantitative techniques in PET-CT imaging," Current Medical Imaging Reviews, vol. 7, No. 3, pp. 216-233, (2011).
Beekman, F. J. et al., "Efficient fully 3-D iterative SPECT reconstruction with Monte Carlo-based scatter compensation," IEEE Transactions on Medical Imaging, vol. 21, No. 8, pp. 867-877 (2002).
Bendriem, B. et al., "PET scatter correction using simultaneous acquisitions with low and high lower energy thresholds," IEEE Nuclear Science Symposium & Medical Imaging Conference, vol. 21, No. 8, pp. 867-877, (1994).
Bentourkia, M., et al., "Energy dependence of scatter components in multispectral PET imaging," IEEE Transactions on Medical Imaging, vol. 14, No. 1, pp. 138-145 (1995).
Bentourkia, M., et al., "Scatter restoration in PET imaging," IEEE Nuclear Science Symposium & Medical Imaging Conference, vol. 2, pp. 1075-1079 (2002).
Burger, C., et al., "PET attenuation coefficients from CT images: Experimental evaluation of the transformation of CT into PET 511-keV attenuation coefficients," European Journal of Nuclear Medicine, vol. 29, No. 7, pp. 922-927 (2002).
Buvat, I., et al., "Scatter correction in scintigraphy: The state of the art," European Journal of Nuclear Medicine, vol. 21, No. 7, pp. 675-694 (1994).

Castiglioni, I., et al., "Scatter correction techniques in 3D PET: A monte carlo evaluation," IEEE Transactions on Nuclear ScienceU, 46(6 Part 3), pp. 2053-2058 (1999).
Chelikani, S., et al., "Optimizing Compton camera geometries," Physics in Medicine and Biology, vol. 49, No. 8, pp. 1387-1408 (2004).
Cheng, J. C., et al., "A scatter and randoms weighted (SRW) iterative PET reconstruction," Medical Physics, vol. 38, No. 6, pp. 3186-3192 (2011).
Conti, M., et al., "Simultaneous reconstruction of scatter and unscattered PET coincidences using TOF and energy information," IEEE Nuclear Science Symposium and Medical Imaging Conference, pp. 2332-2337 (2011).
Cot, A. et al., "Absolute quantification in dopaminergic neurotransmission SPECT using a Monte Carlo-based scatter correction and fully 3-dimensional reconstruction," Journal of Nuclear Medicine, vol. 46, No. 9, pp. 1497-1504 (2005).
Dekemp, R. A. And C. Nahmias, "Attenuation correction in PET using single photon transmission measurement," Medical Physics, vol. 21, No. 6, pp. 771-778 (1994).
Floyd Jr, C. E. et al., "Inverse Monte Carlo as a unified reconstruction algorithm for ECT," Journal of Nuclear Medicine, vol. 27, No. 10, pp. 1577-1585 (1986).
Grootoonk, S. et al., "Correction for scatter in 3D brain PET using a dual energy window method," Physics in Medicine and Biology, vol. 41, No. 12, pp. 2757-2774 (1996).
Guerin, B. and Fakhri, G. E., "Novel scatter compensation of list-mode PET data using spatial and energy dependent corrections," IEEE Transactions on Medical Imaging, vol. 30, No. 3, pp. 759-773 (2011).
Guy, M. J. "Detect—Dual energy transmission estimation CT—for improved attenuation correction in SPECT and PET," IEEE Transactions on Nuclear Science, vol. 45 (3 Part 2), pp. 1261-1267 (1998).
Guzzardi, R. and Licitra G., "A Critical review of Compton imaging," Critical Reviews in Biomedical Engineering, vol. 15, No. 3, pp. 237-268 (1988).
Harrison, R. L., et al., "Dual energy window scatter corrections for positron emission tomography," IEEE Medical Imaging Conference, Santa Fe, pp. 1700-1704 (1992).
Herraiz, J. L., et al., "Fully 3D GPU PET reconstruction," Nuclear Instruments and Methods in Physics Research, Section A: Accelerators, Spectrometers, Detectors and Associated Equipment, vol. 648, (Suppl. 1), pp. S169-S171 (2011).
Kamel, E. M. et al., "Impact of metallic dental implants on CT-based attenuation correction in a combined PET/CT scanner," European Radiology, vol. 13, No. 4, pp. 724-728 (2003).
Kinahan, P. E. et al., "Attenuation correction for a combined 3D PET/CT scanner," Medical Physics, vol. 25, No. 10, pp. 2046-2063 (1998).
Kinahan, P. E. et al., "X-ray-based attenuation correction for positron emission tomography/computed tomography scanners," Seminars in Nuclear Medicine, vol. 33, No. 3, pp. 166-179 (2003).
Levin, C. S. et al., "Monte Carlo correction for the effect of Compton scattering in 3-D pet brain imaging," IEEE Transactions on Nuclear Science, vol. 42, (4 pt 1), pp. 1181-1185 (1995).
Links, J. M., "Scattered photons as "good counts gone bad:" are they reformable or should they be permanently removed from society?" Journal of Nuclear Medicine, vol. 36, No. 1, pp. 130-132 (1995).
Magdics, M., et al., "Scatter estimation for PET reconstruction," IEEE Nuclear Science Symposium & Medical Imaging Conference, Borovets, 6046 LNCS, pp. 77-86 (2011).
Manavaki, R., et al., "Scatter Modeling for 3-D PET List-Mode EM Reconstruction," IEEE Nuclear Science Symposium & Medical Imaging Conference, Norfolk, VA, pp. 1863-1868 (2002).
McQuaid, S. J. and Hutton, B. F. "Sources of attenuation-correction artefacts in cardiac PET/CT and SPECT/CT," European Journal of Nuclear Medicine and Molecular Imaging, vol. 35, No. 6, pp. 1117-1123 (2008).
Meikle, S. R., et al. "Attenuation correction using count-limited transmission data in positron emission tomography," Journal of Nuclear Medicine, vol. 34, No. 1, pp. 143-150 (1993).

(56) References Cited

OTHER PUBLICATIONS

Michel, C., et al., "Online brain attenuation correction in PET: Towards a fully automated data handling in a clinical environment," European Journal of Nuclear Medicine, vol. 15, No. 11, pp. 712-718 (1989).
Msaki, P., et al. "Scatter Degradation and Correction Models for High010Resolution PET," Journal of Nuclear Medicine, vol. 37, No. 12, pp. 2047-2049 (1996).
Nakamoto, Y., et al., "Effects of nonionic intravenous contrast agents at PET/CT imaging: Phantom and canine studies," Radiology, vol. 227, No. 3, pp. 817-824 (2003).
Nakamoto, Y., et al., "PE/CT: Artifacts caused by bowel motion," Nuclear Medicine Communications, vol. 25, No. 3, pp. 221-225 (2004).
Nguyen, M. K., et al., "A new circular-arc Radon transform and the numerical method for its inversion," International Conference of Numerical Analysis and Applied Mathematics 2010. AIP Conference Proceedings, vol. 1281, pp. 1064-1067 (2010).
Nguyen, M. K., et al., "On a Novel Approach to Compton Scattered Emission Imaging," IEEE Transactions on Nuclear Science, vol. 56, No. 3, pp. 1430-1437 (2009).
Nguyen, M.K., et al., "Scattered Radiation Emission Imaging: Principles and Applications," International Journal of Biomedical Imaging, vol. 2011, pp. 1-15 (2011).
Ollinger, J. M., "Mode-based scatter correction for fully 3D PET," Physics in Medicine and Biology, vol. 41, No. 1, pp. 153-176 (1996).
Ollinger, J.M. and Johns, G.C., Mode-based scatter correction in three dimensions [positron emission tomography], Conference Record of the 1992 IEEE Nuclear Science Symposium and Medical Imaging Conference, vol. 2, pp. 1249-1251 (1992).
Osman, M.M., et al. "Respiratory motion artifacts on PET emission images obtained using CT attenuation correction on PET-CT," European Journal of Nuclear Medicine and Molecular Imaging, vol. 30, No. 4, pp. 603-606 (2003).
Polycarpou, I., et al., "Comparative evaluation of scatter correction in 3D PET using different scatter-level approximations," Annals of nuclear medicine, vol. 25, No. 9, pp. 643-649 (2011).
Rafecas, M., et al., "Use of a monte carlo-based probability matrix for 3-D iterative reconstruction of MADPET-II data," IEEE Transactions on Nuclear Science, vol. 51, No. 5, pp. 2597-2605 (2004).
Rehfeld, N. and M. Alber "A parallelizable compression scheme for Monte Carlo scatter system matrices in PET image reconstruction," Physics in Medicine and Biology, vol. 52, No. 12, pp. 3421-3437 (2007).
Roellinghoff, F., et al., "Design of a Compton camera for 3D prompt-imaging during ion beam therapy," Nuclear Instruments and Methods in Physics Research Section A: Accelerators, Spectrometers, Detectors and Associated Equipment, vol. 648, Supplement 1, pp. S20-S23 (2011).
Shao, L., et al., "Composite Dual Window Scattering Correction Technique in PET," IEEE Nuclear Science Symposium & Medical Imaging Conference, pp. 1391-1395 (1993).
Shao, L., et al., "Triple energy window scatter correction technique in PET," IEEE Transactions on Medical Imaging, vol. 13, No. 4, pp. 641-648 (1994).
Siegel, S., and Dahlbom, M., "Implementation and evaluation of a calculated attenuation correction for PET," IEEE Transactions on Nuclear Science, vol. 39, No. 4, pp. 1117-1121 (1992).
Sossi, V., et al., "Noise reduction in the dual energy window scatter correction approach in 3D PET," IEEE Nuclear Science Symposium & Medical Imaging Conference, vol. 4, pp. 1512-1515 (1995).
Thompson, C.J., "The Problem of scatter correction in positron volume imaging," IEEE Transactions on Medical Imaging, vol. 12, No. 1, pp. 124-132 (1993).
Townsend, D.W. and Cherry, S.R., "Combining anatomy and function: The path to true image fusion," European Radiology, vol. 11, No. 10, pp. 1968-1974 (2001).
Van Den Heuvel, O.A., et al., "Attenuation correction of PET activation studies in the presence of task-related motion," Neuroimage, vol. 19, No. 4, pp. 1501-1509 (2003).
Watson, C.C., "New, faster, image-based scatter correction for 3D PET," IEEE Transactions on Nuclear Science, vol. 47, Issue 4, pp. 1587-1594 (2000).
Watson, C.C., et al., Advances in scatter correction for 3D PET/CT,01D IEEE Nuclear Science Symposium Conference Record, vol. 5, pp. 3008-3012 (2004).
Weinzapfel, B.T., and Hutchins, G.D., "Automated PET Attenuation Correction Model for Functional Brain Imaging," Journal of Nuclear Medicine, vol. 42, No. 3, pp. 483-491 (2001).
Zaidi, H. and Koral, K.F., "Scatter modelling and compensation in emission tomography," European Journal of Nuclear Medicine and Molecular Imaging, vol. 31, No. 5, pp. 761-782 (2004).
Zaidi, H., "Comparative evaluation of scatter correction techniques in 3D positron emission tomography," European Journal of Nuclear Medicine, vol. 27, No. 12, pp. 1813-1826 (2000).
Zaidi, H., "Quantitative SPECT: Recent developments in detector response, attenuation and scatter compensation techniques," Physica Medica, vol. 12, No. 3, pp. 101-117 (1996).
Zaidi, H., "Relevance of accurate Monte Carlo modeling in nuclear medical imaging," Medical Physics, vol. 26, No. 4, pp. 574-608 (1999).
Zaidi, H., "Scatter modelling and correction strategies in fully 3-D pet," Nuclear Medicine Communications, vol. 22, No. 11, pp. 1181-1184 (2001).
Zaidi, H., "Statistical reconstruction-based scatter correction: A new method for 3D PET," 22nd Annual International Conference of the IEEE Engineering in Medicine and Biology Society, vol. 1, pp. 86-89 (2000).
Zaidi, H., and Guerra, A.D., "An outlook on future design of hybrid PET/MRI systems," Medical Physics, vol. 38, No. 10, pp. 5667-5689 (2011).
Zaidi, H., and Hasegawa, B., "Determination of the Attenuation Map in Emission Tomography," Journal of nuclear medicine: official publication, Society of Nuclear Medicine, vol. 44, No. 2, pp. 291-315 (2003).
Zaidi, H., and Koral, K.F., "Scatter Correction Strategies in Emission Tomography," Quantitative Analysis in Nuclear Medicine Imaging, pp. 205-235 (2006).
Zaidi, H., and Montandon, M-L., "Scatter Compensation Techniques in PET," PET Clinics, vol. 2, No. 2, pp. 219-234 (2007).
Zaidi, H., et al., "Advances in Attenuation Correction Techniques in PET," PET Clinics, vol. 2, No. 2, pp. 191010217 (2007).
Zaidi, H., et al., An object-oriented Monte Carlo simulator for 3D cylindrical positron tomographs, 01D Computer Methods and Programs in Biomedicine, vol. 58, No. 2, pp. 133-145 (1999).
Zaidi, H., et al., "Attenuation compensation in cerebral 3D PET: effect of the attenuation map on absolute and relative quantitation," European Journal of Nuclear Medicine and Molecular Imaging, vol. 31, No. 1, pp. 52-63 (2004).
Zaidi, H., et al., "Strategies for attenuation compensation in neurological PET studies," Neuroimage, vol. 34, No. 2, pp. 518-541 (2007).

\* cited by examiner

SYSTEMS AND METHODS FOR IMPROVING THE QUALITY OF IMAGES IN A PET SCAN

CROSS-REFERENCE TO RELATED APPLICATIONS

The present application is a U.S. national stage application claiming the benefit of International Application No. PCT/CA2012/050352, which was filed on May 29, 2012, and is hereby incorporated herein by reference in its entirety.

BACKGROUND

In Positron Emission Tomography (PET) systems, particularly those used for scanning small animals and those that construct 3-dimensional images, scattered photons play a significant role because they comprise a large portion of the total number of photons scanned and are the primary contributor to reduced contrast and quantitative accuracy, which leads to poor image reconstruction during the PET scan. 3-dimensional (3D) PET systems are particularly sensitive to scattered photons, and as a result, the PET images appear blurred or contain artifacts.

Previous efforts to eliminate or otherwise minimize the blurring and quantitative inaccuracy created by scattered photons has generally included considerable pre-processing of data and the administration of higher dosages of radioactive material to the subject.

Thus, there exists a need for systems and methods for reducing PET systems' sensitivity to the presence of scattered photons, thereby allowing for more photon data to be used in reconstructing an image, which in turn improves signal-to-noise ratio and the contrast recovery coefficient in PET scanning systems and reduces the amount of radioactive material administered to the subject.

SUMMARY

In an embodiment, a method of reconstructing an image from a positron emission tomography scan may include detecting a plurality of photons selected from scattered photons and unscattered photons by a plurality of detectors, identifying a time interval for each of the plurality of photons by a processing device, matching each of the plurality of photons into a plurality of pairs of coincident photons based upon a substantially simultaneous time interval identified by the processing device, measuring an energy produced by each of the plurality of photons by the plurality of detectors, determining a scattering angle for each pair of coincident photons from an annihilation point relative to the position of the plurality of detectors by the processing device based on the energy produced and reconstructing an image using a reconstruction algorithm, wherein the reconstruction algorithm uses the scattering angle of each pair of coincident photons.

In an embodiment, a method of reconstructing an image from a positron emission tomography scan may include detecting a plurality of photons selected from scattered photons and unscattered photons by a plurality of detectors, identifying a time interval for each of the plurality of photons by a processing device, matching each of the plurality of photons into a plurality of pairs of coincident photons based upon a substantially simultaneous time interval identified by the processing device, measuring an energy produced by each of the plurality of photons by the plurality of detectors, calculating a first circular arc created by all possible positions of a photon of a pair of coincident photons based on the energy produced by the photon by the processing device, calculating a second circular arc created by all possible positions of the photon based on the energy produced by the photon by the processing device, constructing an outline of a subject, constructing one or more lines from a point of detection of one of the unscattered photons to each intersection of the outline of the subject with the first circular arc or the second circular arc, identifying an annihilation area bounded by two or more of the following: the one or more lines, the first circular arc, the second circular arc, and the outline of the subject, identifying the plurality of possible locations of the annihilation point within the annihilation area, based on the energy produced, determining a scattering angle for each pair of coincident photons from a location of the annihilation point relative to the position of the plurality of detectors by the processing device and reconstructing an image using a reconstruction algorithm, wherein the reconstruction algorithm uses the scattering angle of each pair of coincident photons.

In an embodiment, a system for use in reconstructing an image from a positron emission tomography scan may include a processing device and a non-transitory computer-readable storage medium in communication with the processing device, wherein the computer-readable storage medium contains one or more programming instructions that, when executed, cause the processing device to detect a plurality of photons selected from scattered photons and unscattered photons, identify a time interval for each of the plurality of photons, match each of the plurality of photons into a plurality of pairs of coincident photons based upon a substantially simultaneous time interval identified, measure an energy produced by each of the plurality of photons, determine a scattering angle for each pair of coincident photons from an annihilation point relative to the position of the plurality of detectors based on the energy produced, measure an energy produced by a plurality of scattered photons from an annihilation event, match a plurality of pairs of coincident scattered photons based upon the energy measured, determine a scattering angle of each pair of coincident scattered photons from the plurality of pairs of coincident scattered photons and reconstruct an image using a reconstruction algorithm, wherein the reconstruction algorithm uses the scattering angle of each pair of coincident scattered photons.

In an embodiment, a positron emission tomography scanner may have a plurality of detectors, a processing device in operable communication with the plurality of detectors and a non-transitory computer-readable storage medium in communication with the processing device, wherein the computer-readable storage medium contains one or more programming instructions that, when executed, cause the processing device to direct the plurality of detectors to detect a plurality of photons selected from scattered photons and unscattered photons, identify a time interval for each of the plurality of photons, match each of the plurality of photons into a plurality of pairs of coincident photons based upon a substantially simultaneous time interval identified, direct the plurality of detectors to measure an energy produced by each of the plurality of photons, based on the energy produced, determine a scattering angle for each pair of coincident photons from an annihilation point relative to the position of the plurality of detectors and reconstruct an image using a reconstruction algorithm, wherein the reconstruction algorithm uses the scattering angle of each pair of coincident photons.

DETAILED DESCRIPTION

Figure 1:
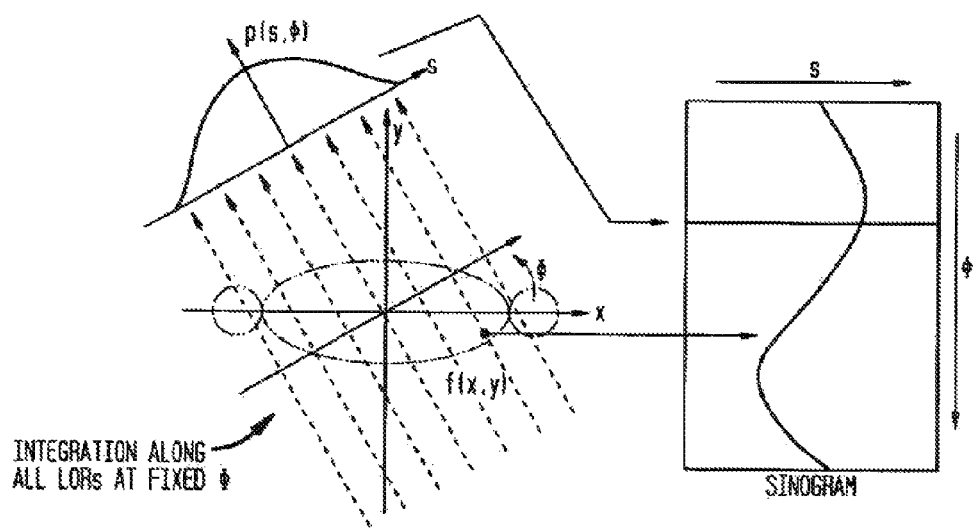
FIG. 1 depicts a diagram illustrating a relationship between a PET projection and a sinogram.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The following terms shall have, for the purposes of this application, the respective meanings set forth below.

As used herein, the terms "sum," "product" and similar mathematical terms are construed broadly to include any method or algorithm in which a single datum is derived or calculated from a plurality of input data.

A "computing device" refers to a computer, a processing device and/or any other component, device or system that performs one or more operations according to one or more programming instructions. The computing device may be integrated within a PET system or may be an individually functioning unit that is in operable communication with the PET system. An illustrative computing device is described in FIG. 9.

Also as used herein, the phrase "reconstructing an image" is not intended to exclude embodiments in which data representing an image is generated, but a viewable image is not. Therefore, as used herein, the term "image" broadly refers to both viewable images and data representing a viewable image. However, many embodiments generate (or are configured to generate) at least one viewable image.

Additionally, while the present disclosure refers in detail to a PET system, particularly a three-dimensional PET system, those skilled in the art will recognize that other modalities such as, for example, PET/ultrasound, PET/Magnetic Resonance Imaging (PET/MRI), PET/Electron Beam CT (PET/EBCT), PET/Computed Tomography (PET/CT), Single Photon Emission Computed Tomography (SPECT) may be used without departing from the scope of the present disclosure. Additionally, systems are contemplated in both medical settings and non-medical settings such as, for example, an industrial setting or a transportation setting.

In PET imaging, a positron-emitting radionuclide is introduced into the object to be imaged via injection, inhalation, ingestion or the like. Once the positron-emitting radionuclide has been administered, its physical and bio-molecular properties cause the agent to concentrate at specific locations within the subject's body. Clinically significant factors in this distribution may include an actual spatial distribution of the radionuclide, an intensity of the region of accumulation of the radionuclide, and kinetics of the process from administration to elimination of the radionuclide. During this process, a positron emitter attached to the positron-emitting radionuclide will emit a number of positrons, which may vary according to certain physical properties of the radionuclide, such as, for example, half-life, branching ratio, and the like.

When an emitted positron collides with an electron, an annihilation event occurs, which destroys both the positron and the electron. Typically, the annihilation event will produce a pair of gamma ray photons at 511 keV, wherein the two photons generally travel in opposite directions (i.e., substantially 180 degrees apart from each other).

The PET system may utilize a plurality of detectors to detect the two photons, and then use a software program to draw a line between their respective locations (i.e., the line-of-response (LOR)) to determine a likely location of the annihilation event. While this process will only identify a single line of possible interaction, by drawing a large number of those lines from as many photons as possible, the original distribution can be estimated.

In addition to determining the location of the annihilation event, a time-of-flight (TOF) calculation also includes identifying a time coincidence between the detection of the two 511 keV gamma photons in the two oppositely disposed detectors (i.e, the photon emissions are detected substantially simultaneously by each detector).

PET systems may use the plurality of detectors positioned across from one another to detect the photons emitting from the annihilation events. In some PET systems, a ring of detectors may be used to detect photons at every possible angle. Thus, a series of scanners arranged in a substantially cylindrical manner may be used to detect as many photons as possible. In other PET systems, the scanners may be arranged in a series of partial rings that are capable of rotating about a subject to detect as many photons as possible at every possible angle.

After being sorted into parallel projections, the LORs defined by the coincidence events are used to reconstruct a three-dimensional distribution of the positron-emitting radionuclide within the subject. In two-dimensional PET systems, each 2D transverse section or "slice" of the radionuclide distribution is reconstructed independently of adjacent sections. In fully three-dimensional PET systems, the data are sorted into sets of LORs, where each set is parallel to a particular detector angle, and therefore represents a two dimensional parallel projection $p(s, \phi)$ of the three dimensional radionuclide distribution within the subject, where s corresponds to the distance of the imaging plane perpendicular to the scanner axis and $\phi$ corresponds to the angle of the detector plane with respect to the x axis in $(x, y)$ coordinate space. In other words, $\phi$ corresponds to a particular LOR direction. Coincidence events are integrated or collected for each LOR and stored as a sinogram. In this format, a single fixed point in f (x,y) traces a sinusoid in the sinogram. In each sinogram, there is one row containing the LORs for a particular azimuthal angle φ; each such row corresponds to a one-dimensional parallel projection of the tracer distribution at a different coordinate along the scanner axis, as shown in FIG. 1.

An event may be registered if both detectors detect an annihilation photon within a coincidence time window τ. A pair of detectors may be sensitive only to coincidence events occurring in the volume between the two detectors, thereby eliminating the need for physical collimation, and thus significantly increasing sensitivity. Accurate corrections may be made for the self-absorption of photons within the subject (i.e., attenuation correction) so that accurate measurements of tracer concentration can be made.

The number of coincidences detected per second within a field of view (FOV) of a detector is known as the count rate of the detector. The count rate at each of two oppositely disposed detectors (e.g., detector A and detector B), may be referred to as singles counts (e.g., singles $S_A$ and $S_B$). The time required for a gamma photon to travel from its point of origin to a point of detection is referred to as the time of flight (TOF) of the gamma photon. TOF is dependent upon the speed of light c and the distance traveled. A time coincidence, or coincidence event, is identified if the time difference between the arrival of signals in a pair of oppositely disposed detectors is within the coincidence time window Σ. In conventional PET systems, the coincidence detection time window τ is wide enough so that an annihilation event occurring anywhere within the object would produce annihilation gamma photons reaching their respective detectors within the coincidence window. Coincidence time windows of 4.5-12 nanoseconds are common for conventional PET systems, and may be determined by the time resolution capabilities of the detectors and electronics.

Septumless PET systems, or 3D PET systems (i.e., without interplane septa) currently constitute a large percentage of the total market for PET imaging. Because of the lack of interplane septa, scattered events (i.e., annihilation photons undergoing Compton scattering before reaching the detector) may represent a large portion of the measured data (e.g., up to 50% or more in clinical studies).

Figure 2:
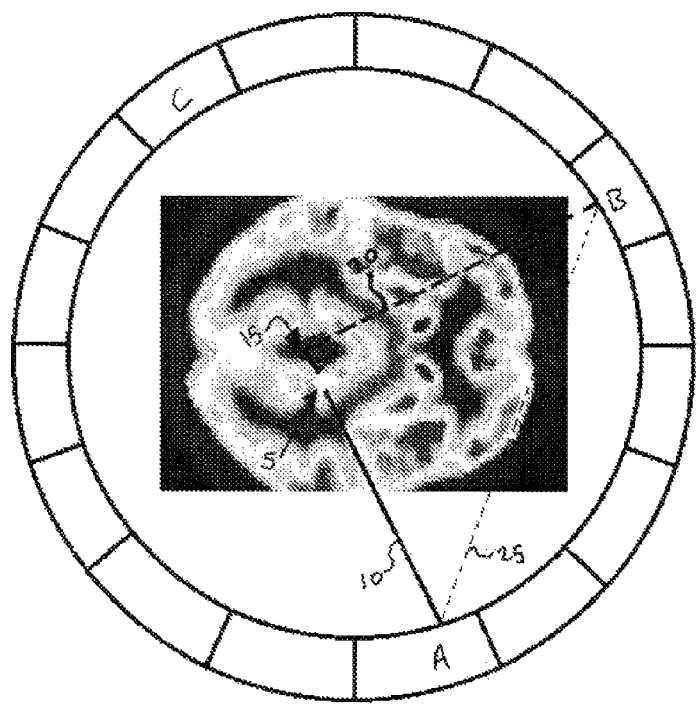
FIG. 2 depicts a diagram illustrating a single scatter model for PET imaging using a plurality of detectors arrange in a ring format, in accordance with an embodiment.

As shown in FIG. 2, the annihilation event occurring at an emission point 5 produces two oppositely traveling photons along LOR 10. At least one of the photons, however, may undergo Compton scattering, such as the scatter of the photon at a scatter point 15, which changes the photon travel direction to path 20. The first photon, which remains unscattered in this instance, is detected by detector A. The second photon, which is scattered in this instance, is detected by detector B because it has been redirected off of its normal path to detector C. Thus, without the scatter correction as presented herein, the PET system would recognize the scattered photon as an unscattered photon, and would determine an incorrect LOR 25.

Figure 3:
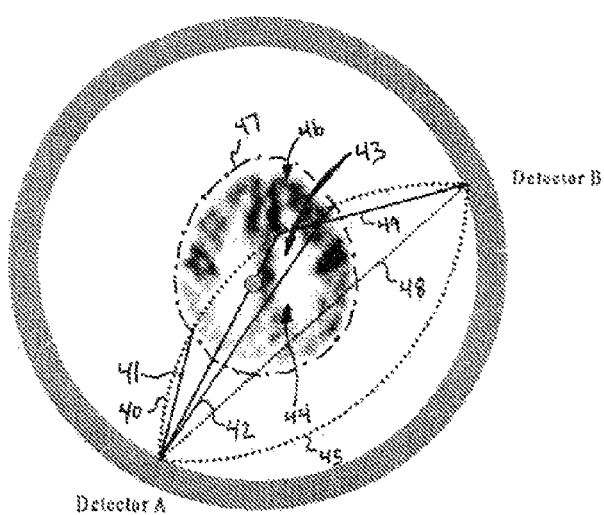
FIG. 3 depicts a diagram of the two arcs created by the PET system in response to detecting a single scatter event according to an embodiment.

In an embodiment, a system and method for measuring scattered photons and reconstructing an image based upon the measuring in a PET system is disclosed. Generally, the system may measure the respective energies of a plurality of pairs of coincident photons and then use the measured energies to create a two arc model for each pair of coincident photons for use in image reconstruction, as shown in FIG. 3. The two arc model may comprise a first arc 40 and a second arc 45. Each of the arcs 40, 45 may extend between the two detectors that measure the photons, such as in the present example, Detector A and Detector B.

Each of the arcs 40, 45 may be a graphical representation created by the PET system that indicates all of the possible locations of a point of scatter of the scattered photon. In 3D PET systems, the arc may be rotated 360 degrees about the axis 48 between the two detectors A, B to define a bounded volume. In 2D PET systems, the two arcs 40, 45 may define a first annihilation area bounded by the two arcs 40, 45.

In addition to the two arcs, the PET system may also determine a second annihilation area 46 that is bounded by an outline 47 of the subject's body. This area 46 may generally represent locations within the subject's body, whereas everything outside the outline 47 is located outside the subject's body. Furthermore, the second annihilation area 46 may have certain areas that overlap the first annihilation area defined by the two arcs 40, 45. The PET system may determine the second annihilation area 46 by any method now known or later developed. Examples of methods that may be used to determine the second annihilation area 46 may include, but are not limited to, use of an external x-ray source to calculate the attenuation of the subject's body, use of an optical system (e.g., laser-based systems or photogrammetric systems, use of a PET/CT or a PET/MRI system, wherein the CT or the MRI outline is used, approximating the subject outline based on an early iteration without subject outline constraints, or use of a geometric shape (e.g., an ellipsis) that encompasses the subject, wherein the size of the geometric shape may be chosen based on a measurement or an estimation of the size of the subject.

Since the annihilation event can only happen within the body of the subject, the PET system may recognize any number of possible annihilation event locations inside the second annihilation area 46 and discard any possible annihilation event locations that are outside the annihilation area 46. Furthermore, the PET system may recognize that the annihilation event occurred within the area bounded by the two arcs 40, 45. The PET system may combine the information obtained and eliminate any possible positions that occur outside the first annihilation area bounded by the two arcs 40, 45 and the second annihilation area 46. Thus, areas that are bounded by the two arcs 40, 45 and not bounded by the subject's body 46, as well as areas bounded by the subject's body 46 but not bounded by the two arcs 40, 45 may be eliminated as possible locations of the annihilation event. However, the annihilation area 44 that is bounded by the two arcs 40, 45 and the subject's body 46 may be recognized as containing the annihilation point.

In addition to area defined by the two arcs 40, 45 and the second annihilation area 46, the PET system may further narrow the area containing the annihilation point by drawing a plurality of straight lines between the point where the unscattered photon is detected to each locus of an intersection of the two arcs 40, 45 with the outline 47 of the subject's body. In the example shown in FIG. 3, each locus of the intersection of the two arcs 40, 45 and the outline 47 of the subject's body both occur on arc 40. However, it is anticipated that each locus may occur on either arc, or even both arcs. Thus, the two lines 41, 42 extend from the point of detection on Detector A to each intersection of the outline 47 and the arc 40. As a result, a third annihilation area 43 is formed. The PET system may recognize that the exact location of the annihilation event will be within the third annihilation area 43. Thus, the PET system may use that information in conjunction with one or more reconstruction algorithms to further attempt to discern an exact location of the annihilation event, as described in more detail herein.

In an embodiment, a Compton equation may be used to determine a scattering angle, which, in turn, may be used to determine two symmetrically circular arcs (TCA) that extend between the two detectors sensing a pair of coincident photons, wherein one photon is scattered and the other remains unscattered. The Compton equation for a PET system is as follows:

$$E_2 = \frac{E}{2 - \cos\theta}$$

where $E_s$, is the scattered photon energy, E is the unscattered photon energy (0.511 MeV), and $\theta$ is the scattering angle of the unscattered photon.

The size and shape of the area encompassed by the TCA is a function of the scattering angle and the detector position. In the limit where the scattering angle approaches zero and the energy of the scattered photon approaches 511 keV, the shape of the area encompassed by the TCA approaches the LOR for unscattered photons. This approach therefore does not distinguish explicitly between scattered and unscattered photons.

Figure 4:
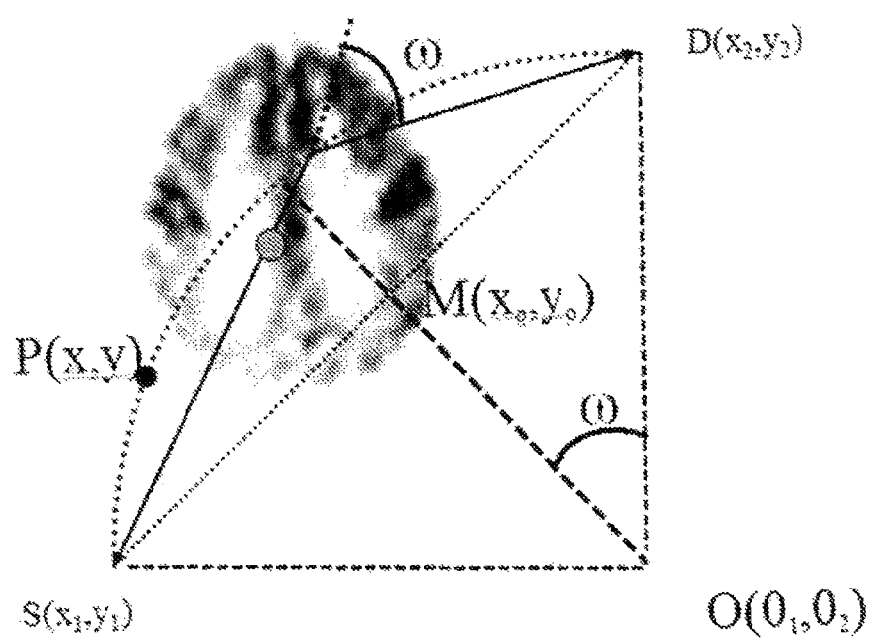
FIG. 4 depicts a graphical diagram of measuring a circular arc from a single scatter model according to an embodiment.

FIG. 4 depicts a circular arc $\widehat{SD}$ that is created by a PET system in measuring all of the possible locations of a point of scatter of a scattered photon, in accordance with an embodiment.

M may represent a midpoint of line SD wherein the coordinates of midpoint M are represented by equations (1) and (2):

$$x_0 = \frac{x_2 + x_2}{2} \quad (1)$$

$$y_0 = \frac{y_2 + y_2}{2} \quad (2)$$

Furthermore, a straight line distance between S and D may be calculated as shown in Equation (3):

$$SD = \sqrt{(x_1 - x_2)^2 + (y_1 - y_2)^2} \quad (3)$$

In addition, circle O (where O represents the center of the circle) may have a radius represented by Equation (4):

$$r = \frac{SD}{2\sin\omega} \quad (4)$$

Using the above equations, it can be shown that line SD and line OM are perpendicular to each other, as illustrated in Equation (5):

$$(x_1 - x_2)(o_1 - x_2) + (y_1 - y_2)(o_2 - y_0) = 0 \quad (5)$$

Furthermore, the length of line OM is represented by Equation (6):

$$OM = \sqrt{(o_1 - x_o)^2 + (o_2 - y_o)^2} = r * \cos\omega \quad (6)$$

In instances where $X_1$ is not equal to $X_2$, the coordinates of the center of the circle O may be represented by Equations (7) and (8), or alternatively by Equations (9) and (10):

$$o_1 = x_0 - \frac{(y_1 - y_2) * \cos\omega}{2 * \sin\omega} \quad (7)$$

$$o_2 = y_0 + \frac{(x_1 - x_2) * \cos\omega}{s * \sin\omega} \quad (8)$$

$$o'_1 = x_0 + \frac{(y_1 - y_2) * \cos\omega}{2 * \sin\omega} \quad (9)$$

$$o'_2 = y_0 - \frac{(x_1 - x_2) * \cos\omega}{2 * \sin\omega} \quad (10)$$

Conversely, in instances where $X_1$ is equal to $X_2$, the coordinates of the center of the circle O may be represented by Equations (11) and (12) or alternatively by Equations (13) and (14):

$$o_1 = x_0 + r * \cos\omega \quad (11)$$

$$o_2 = y_0 \quad (12)$$

$$o'_1 = x_0 - r * \cos\omega \quad (13)$$

$$o'_2 = y_0 \quad (14)$$

Thus, the first annihilation area bounded by the two arcs may be represented by Equation (15):

$$(x - o_1)^2 + (y - o_2)^2 \le r^2 \ \& \ (x - o'_2)^2 + (y - o'_2)^2 \le r^2 \quad (15)$$

Figure 5:
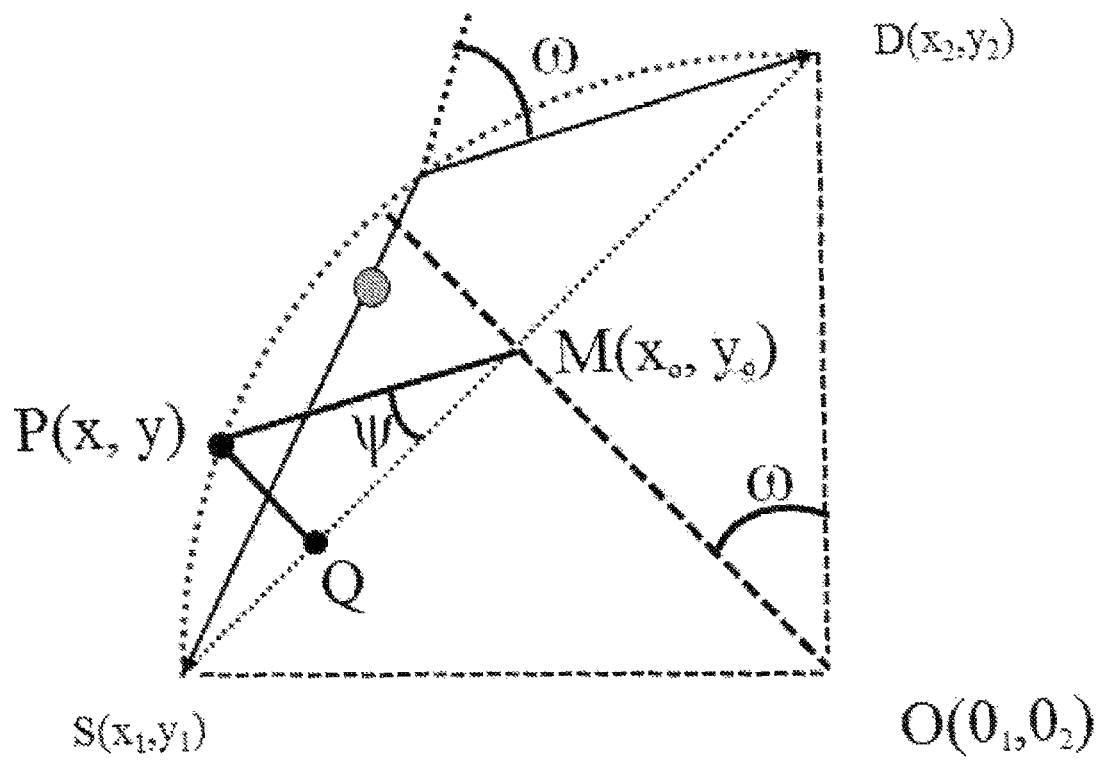
FIG. 5 depicts an alternative graphical diagram of measuring a circular arc from a single scatter model according to another embodiment.

FIG. 5 depicts an alternative measurement of circular arc $\widehat{SD}$ that is created by a PET system in measuring all of the possible locations of a point of scatter of a scattered photon, in accordance with another embodiment. M may represent a midpoint of line SD and may have coordinates as shown in Equations (1) and (2). In this embodiment, P may represent any point in the plane. Thus, the length of line PM may be calculated by Equation (16):

$$PM = \sqrt{(x - x_0)^2 + (y - y_0)^2} \quad (16)$$

Line PM and line SD may define an angle, as represented by Equation (17):

$$\cos\psi = \frac{|(x - x_2)(x_1 - x_2) + (y - y_0)(y_1 - y_2)|}{\sqrt{(x - x_0)^2 + (y - y_0)^2} * \sqrt{(x_1 - x_2)^2 + (y_1 - y_2)^2}} \quad (17)$$

Thus, when drawing a line from point P to point Q on line SD, wherein the PQ is perpendicular to SD, the length of line PQ can be calculated with Equation (18):

$$PQ = PM * \sin\psi \quad (18)$$

Furthermore the length of line QM can be calculated with Equation (19):

$$QM = PM * \cos\psi \quad (19)$$

Thus, the length of line SD is found by use of Equation (20):

$$SD = \sqrt{(x_2 - x_2)^2 + (y_2 - y_2)^2} \quad (20)$$

From Equation (20), the radius of circle O can be found with Equation (21):

$$r = \frac{SD}{2\sin\omega} \quad (21)$$

Figure 6:
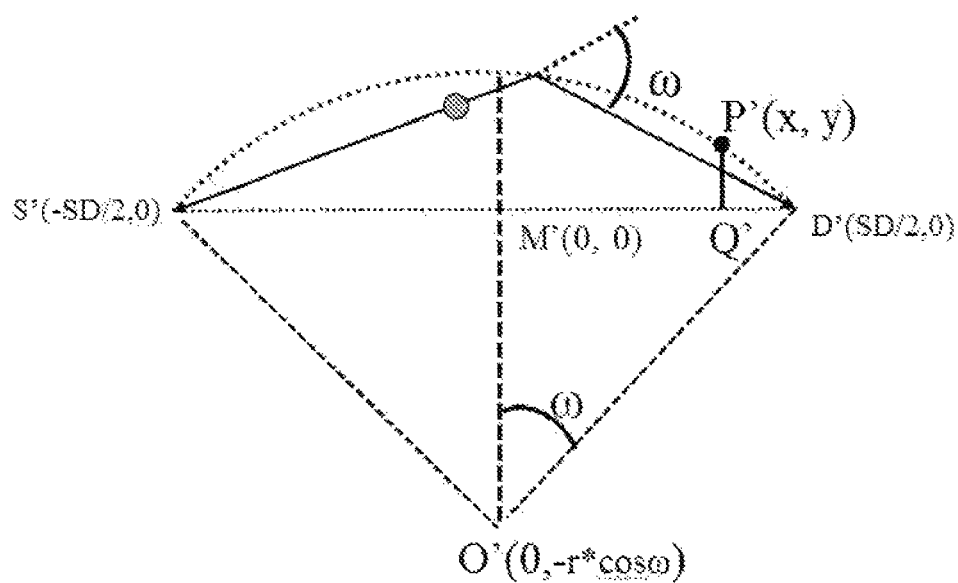
FIG. 6 depicts a rotated view of the graphical diagram of FIG. 5.

Then, as depicted in FIG. 6, the arc is rotated so that line SD is located upon the x-axis at a location that allows point the middle point M to be located at the origin (0,0). Thus, the coordinates of S' are (−SD/2, 0) and the coordinates of D' are (SD/2, 0). The coordinates of the center of the circle O are (0, −r×cos ω, where ω represents the scattering angle created by the y axis and line OD. Since point P' is located on the circle O, the coordinates for point P' may be calculated using Equation (22):

$$x^2 + (y + r*\cos\omega)^2 = r^2 \quad (22)$$

Accordingly, the length of line P'Q' can be found with Equation (23):

$$P'Q' = y = \sqrt{r^2 - x^2} - r*\cos\omega \quad (23)$$

The other root of the equation may be ignored because of its physical meaning, thereby the constraint for any point P in the plane located within the two circular arcs giving Equation (24):

$$PQ \leq \sqrt{r^2 - QM^2} - r*\cos\omega \quad (24)$$

In yet another alternative embodiment, a calculation of a circular arc that is created by a PET system in measuring all of the possible locations of a point of scatter of a scattered photon may involve first assuming that the two detectors that detect the photons are defined by angles $\Omega_1$ and $\Omega_2$ on a circle of radius R about an origin O. The length of a chord that connects the two detectors may be given be Equation (25):

$$2R\sin\left(\frac{\Omega_2 - \Omega_1}{2}\right) \quad (25)$$

If the same chord that connects the two detectors is labeled 2U, then Equation (25) is rewritten as Equation (26):

$$U = R\sin\left(\frac{\Omega_2 - \Omega_1}{2}\right) \quad (26)$$

Thus, a vector drawn from the origin O to the center of the chord may have a magnitude given by Equation (27):

$$r_1 = R\cos\left(\frac{\Omega_2 - \Omega_1}{2}\right) \quad (27)$$

That vector $V_1$ may further be given in radial coordinates $V_1$ ($r_1$, $\phi$) by Equation (28):

$$V_1\left(R\cos\left(\frac{\Omega_2 - \Omega_1}{2}\right)\frac{\Omega_1 + \Omega_2}{2}\right) \quad (28)$$

The implicit equation in (x,y) which describes the two circular arcs in terms of the scattering angle θ and the radial distance between the detectors U when the center of the two circular arcs is located at the origin O is given by Equation (29):

$$\theta = \pi - \arctan\left(\frac{U - y}{x}\right) - \arctan\left(\frac{U + y}{x}\right) \quad (29)$$

The relationship between the scattering angle θ and the scattered photon energy $E_s$ in a PET system is given by Equation (30):

$$E_s = \frac{E}{2 - \cos\theta} \quad (30)$$

where E=0.511 MeV.

Solving for θ gives Equation (31):

$$\theta = \left\{\pi - \arccos\frac{1}{E_s}(E - 2E_s) + 2\pi k \,\middle|\, k \in Z\right\} \quad (31)$$

which allows for a relation of the equation describing the x,y position of the two circular arcs to the scattered photon by Equation (32):

$$\arccos\frac{1}{E_s}(E - 2E_s) = \arctan\left(\frac{U - y}{x}\right) + \arctan\left(\frac{U + y}{x}\right) \quad (32)$$

Writing Equation (32) in radial coordinates $V_2(r_2, \tau)$ where $$\tan\tau = \frac{x}{y}$$

and $$r_2 = \sqrt{x^2 + y^2} = x\sqrt{1 + \frac{1}{\tan^2 \tau}}$$

gives Equation (33):

$$\arccos\frac{1}{E_s}(E - 2E_s) = \arctan\left(\frac{U\sqrt{1 + \frac{1}{\tan^2\tau}}}{r_2} - \frac{1}{\tan\tau}\right) + \arctan\left(\frac{U\sqrt{1 + \frac{1}{\tan^2\tau}}}{r_2} + \frac{1}{\tan\tau}\right) \quad (33)$$

When Equation (33) is solved for $r_2$ and by substituting for U, Equation (34) results:

$$r_2 = \frac{1}{2}\mathrm{RE}_s\left(\sin\left(\frac{\Omega_1 - \Omega_2}{2}\right)\right)\frac{\tan^2\tau - 1}{\tan^4\tau - 1}\sqrt{-\frac{1}{E_s^2}(E^2 - 4EE_s + 3E_s^2)} \quad (34)$$

$$\frac{2\sqrt{-(\tan^2\tau + 1)(E^2 - 4EE_s - E_s^2\tan^2\tau + 3E_s^2)} + 2E(\tan^2\tau)\sqrt{\frac{1}{\tan^2\tau}(\tan^2\tau + 1)} - 4E_s(\tan^2\tau)\sqrt{\frac{1}{\tan^2}}}{E^2 - 4EE_s + 3E_s^2}$$

The vector $V_2$ which describes the vector from the center of the chord to the circular arc is given by $V_2(r_2, \tau)$. Summing the vectors $V_1$ and $V_2$ enables the two circular arcs to be calculated for any pair of detected photons and scattered photon energy.

Accordingly, the PET system may recognize that the annihilation point may be positioned at a location that is within the area (2D systems) or volume (3D systems) bounded by the arcs 40, 45 and the area bounded by the subject's body 46, as shown in FIG. 3. Thus, in instances where an annihilation event has produced a scattered photon and an unscattered photon, and further wherein Detector A detects the scattered photon and Detector B detects the unscattered photon, the PET system will measure the energies of the two photons to create a model containing the arcs 40, 45 and determine that the annihilation event occurred at a location along LOR 49 within the third annihilation area 43.

Figure 7:
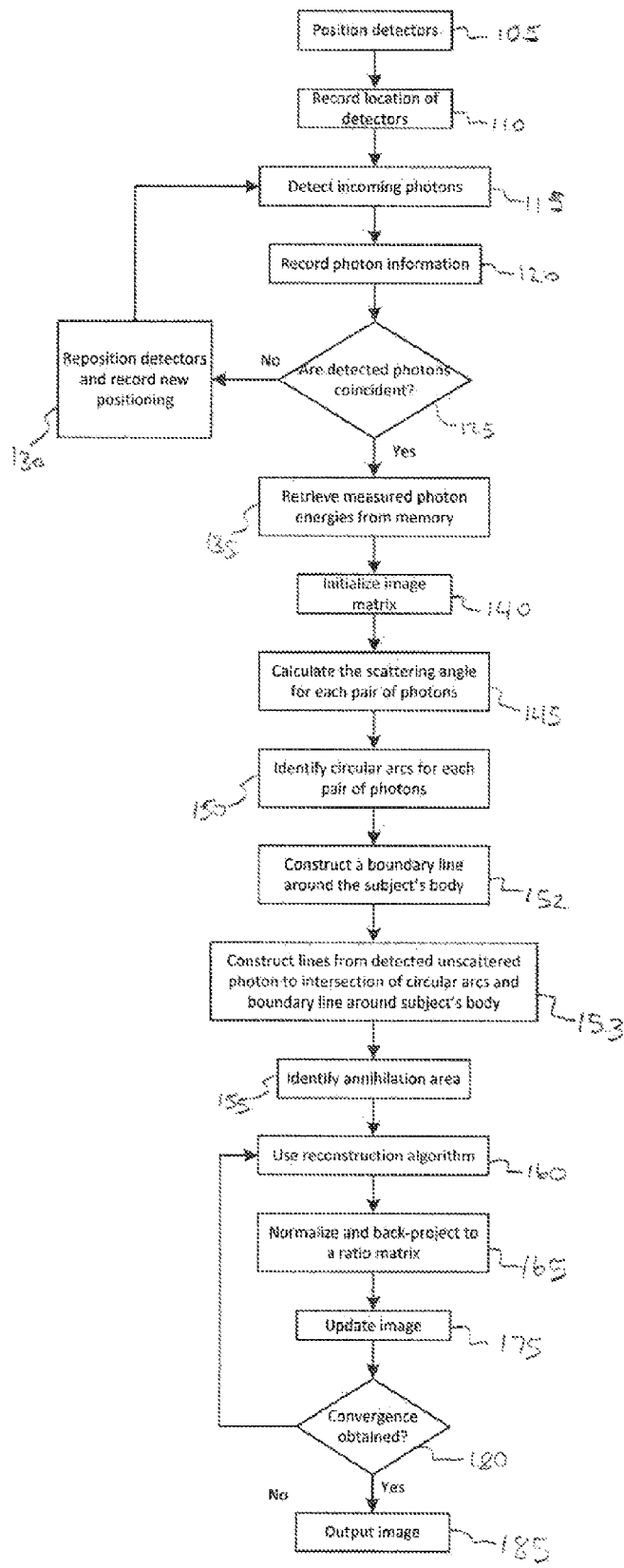
FIG. 7 depicts a flow diagram of an illustrative method of reconstructing an image from a PET scan according to an embodiment.

FIG. 7 depicts a flow diagram of a process used according to an embodiment to detect photons produced from an annihilation. A first step may be to position the detectors 105. Positioning may be in any manner necessary to obtain a desired scan of a target object. Once the detectors have been positioned, the location of the detectors may be recorded 110 so that locations of annihilations, as described herein, can be located with respect to the detectors.

Once the detectors have been positioned and their locations have been recorded, the PET system may begin detecting incoming photon activity 115. Thus, each time a detector senses a photon, the system may record information about the photon 120. Information about the photon may include, but is not limited to, a time at which the photon was detected, a location of the detector when the photon was detected, a location on the detector where the photon was sensed, an energy produced by the photon and/or the like.

The PET system may compare the detection times of the detected photons and make a determination as to whether a given pair of photons are coincident 125. This determination may be based upon a matching process, wherein a pair of photons that are detected at substantially the same time may be deemed coincident. Additionally, photons that are detected within about 4.5 nanoseconds to about 12 nanoseconds of each other may be deemed to be sufficiently coincident to be matched as a pair. In an embodiment, photons that are detected within about 5 nanoseconds of each other may be deemed to be sufficiently coincident to be matched as a pair. In another embodiment, photons that are detected within about 7.5 nanoseconds of each other may be deemed to be sufficiently coincident to be matched as a pair. In another embodiment, photons that are detected within about 10 nanoseconds of each other may be deemed to be sufficiently coincident to be matched as a pair. The system may continue to detect additional incoming photons, and may optionally reposition the detectors and record their new locations 130.

If a pair of photons has been deemed coincident, the PET system may analyze the recorded energies of the photons, which may optionally be retrieved from memory 135. The system may initialize an image matrix 140, which provides starting values for a scanned image. The image matrix may generally be, for example, a mathematical matrix, wherein each pixel of the image is initially set to a value. As the reconstruction progresses, the image is updated to represent the distribution of activity. The sizes of the matrix may reduce any computation burden and increase any spatial resolution.

Using the image matrix, the PET system may begin the image reconstruction process by first calculating the scattering angle for each pair of coincident photons 145, as described in more detail herein. With the scattering angle calculated, the PET system may then identify the circular arcs from the measured energies of the photons 150. The PET system may also construct a boundary line around the subject's body 152 and then construct one or more lines from the detection point of the unscattered photon to the intersection of the circular arcs with the boundary line 153. The area (2D systems) or the volume (3D systems) bounded by the arcs, the subject's body boundary and the one or more lines may be used to identify possible annihilation points therein 155.

Armed with the information regarding the location of possible annihilation points, the system may use one or more reconstruction algorithms 160 now known or later developed to further narrow the possibilities for annihilation point locations and reconstruct the image. Examples of reconstruction algorithms may include, but are not limited to, a Maximum-Likelihood Expectation-Maximum (MLEM) algorithm, an ordered subset expectation maximization (OSEM) algorithm, a maximum a posteriori expectation maximization (MAPEM) algorithm, a filtered back projection (FBP) algorithm, a conjugate gradient (CG) algorithm and a coincidence-list-ordered sets expectation-maximization (CLOSEM) algorithm.

The location of each annihilation point may be estimated from each pair of coincident photons (whether scattered or unscattered) and by using one or more reconstruction algorithms, the PET system may reconstruct a distribution of activity. If the reconstruction is carried out using a Maximum Likelihood Expectation Algorithm (MLEM), this process may include the normalization of the image matrix, and the back-projection of the sum of the pixel values with the annihilation areas for each coincident pair of photons into a ratio matrix 165. The ratio matrix may store a backprojected value for each pair of photons in each iteration. After all of the pairs have been calculated, the ratio matrix may be used to update the image matrix. The ratio matrix may be re-initialized (i.e., set to zero), and the process may repeat. The reconstructed image may then be updated with the new information 175, and the PET system may then make a determination as to whether convergence has been obtained 180. Convergence may be obtained by any methods of estimation now known or later developed. One such example of a method may include evaluating noise level of an image and stop iterating once the noise level has reached a minimum threshold.

If convergence has not been obtained, the system may use one or more additional reconstruction algorithms 160 and repeat the process. If convergence has been obtained, the image may be outputted 185 to a device that is operably connected to the PET system, such as, for example, a computer monitor, a printer and/or the like.

Figure 8:
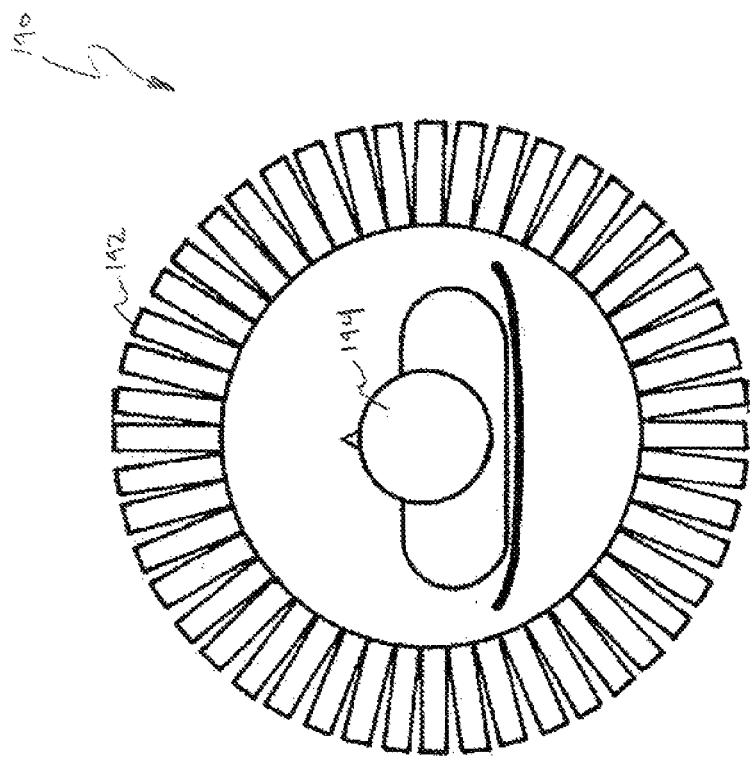
FIG. 8 depicts an illustrative cross-sectional view of a PET system according to an embodiment.

FIG. 8 depicts an illustrative cross-sectional view of a PET system 190. The PET system 190 may generally have a plurality of detectors 192 arranged in a circular manner about a subject 194, such as a system where the detectors 192 are arranged on the inside surface of a cylindrical structure, and the subject 194 is placed within the cylinder so that the detectors 192 surround the subject 193 on all sides. Each of the detectors 192 may further be rotatable around the subject 194. Thus, each of the detectors 192 may have an ability to obtain readings, as described in more detail herein, at any position 360 degrees around the subject 194. While the detectors 192 shown herein are rectangular in shape, those skilled in the art will recognize that the detectors 192 may be any shape without departing from the scope of this disclosure. The detectors 192 may further be connected to a number of other components, such as the components disclosed in FIG. 9.

Figure 9:
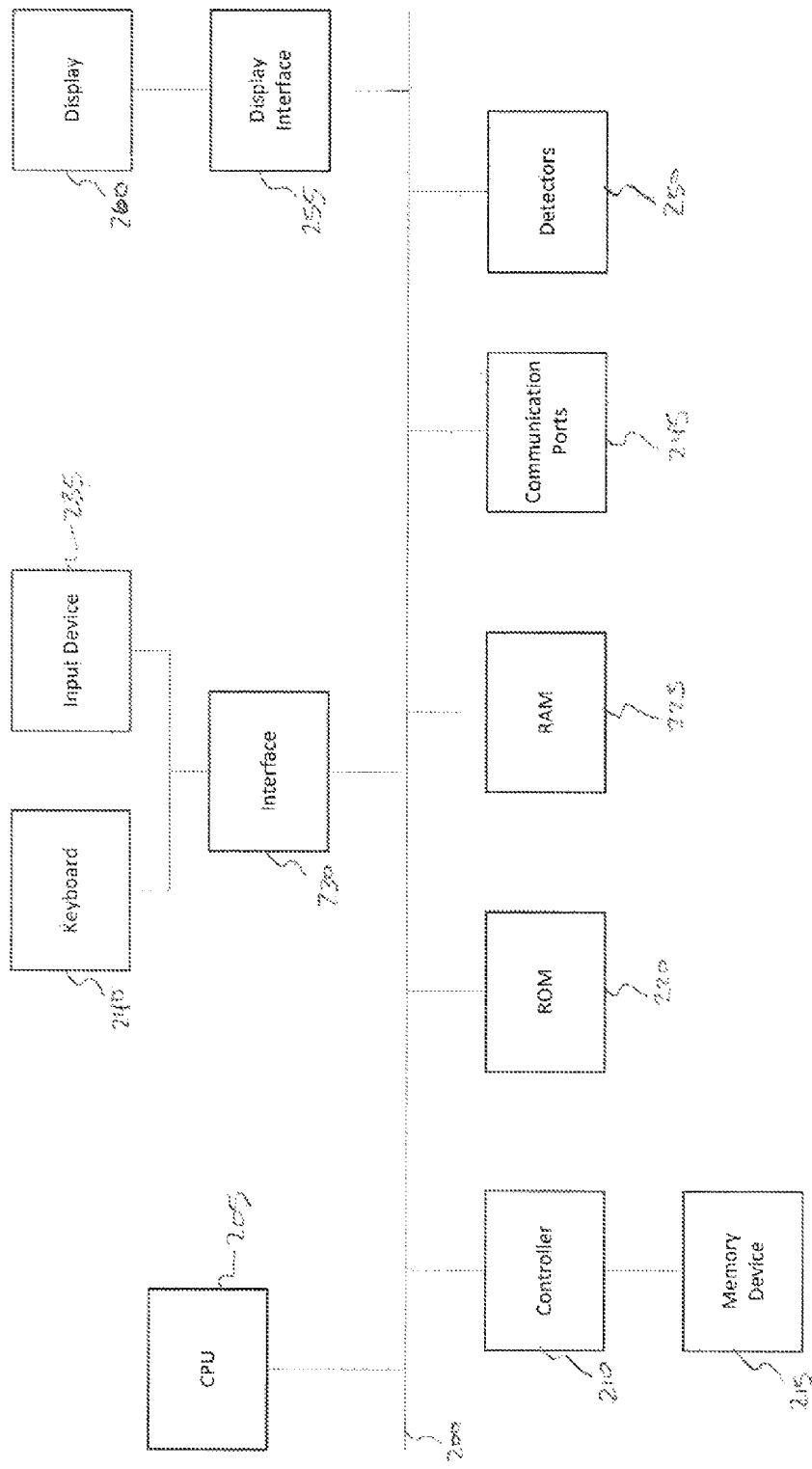
FIG. 9 depicts a block diagram of illustrative internal hardware that may be used to contain or implement program instructions according to an embodiment.

FIG. 9 depicts a block diagram of illustrative internal hardware that may be used to contain or implement program instructions, such as the process steps discussed above in reference to FIG. 7, according to embodiments. A bus 200 serves as the main information highway interconnecting the other illustrated components of the hardware. CPU 205 is the central processing unit of the system, performing calculations and logic operations required to execute a program. The CPU 205, alone or in conjunction with one or more of the other elements disclosed herein, is an illustrative processing device, computing device or processor as such terms are used within this disclosure. Read only memory (ROM) 220 and random access memory (RAM) 225 constitute illustrative memory devices (i.e., processor-readable non-transitory storage media).

A controller 210 interfaces with one or more optional memory devices 215 to the system bus 200. These memory devices 215 may include, for example, an external or internal DVD drive, a CD ROM drive, a hard drive, flash memory, a USB drive or the like. As indicated previously, these various drives and controllers are optional devices.

Program instructions, software or interactive modules for providing the interface and performing any querying or analysis associated with one or more data sets may be stored in the ROM 220 and/or the RAM 225. Optionally, the program instructions may be stored on a tangible computer readable medium such as a compact disk, a digital disk, flash memory, a memory card, a USB drive, an optical disc storage medium, such as a Blu-ray™ disc, and/or other non-transitory storage media.

An optional display interface 255 may permit information from the bus 200 to be displayed on the display 260 in audio, visual, graphic or alphanumeric format. Communication with external devices, such as a print device, may occur using various communication ports 245. An illustrative communication port 245 may be attached to a communications network, such as the Internet or an intranet.

The hardware may also include an interface 230 which allows for receipt of data from input devices such as a keyboard 240 or other input device 235 such as a mouse, a joystick, a touch screen, a remote control, a pointing device, a video input device and/or an audio input device.

The hardware may also include one or more detectors 250 connected to the bus 200, which allow the system to detect photon activity, as described in more detail herein. The one or more detectors 250 may optionally be connected to the communications ports 245 in instances where the hardware is employed at a location that is remote to the location of the detectors 250.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of reconstructing an image from a positron emission tomography scan, comprising:
   detecting a plurality of photons selected from scattered photons and unscattered photons by a plurality of detectors;
   identifying a time interval for each of the plurality of photons by a processing device;
   matching each of the plurality of photons into a plurality of pairs of coincident photons based upon a substantially simultaneous time interval identified by the processing device;
   measuring an energy produced by each of the plurality of photons by the plurality of detectors;
   calculating a first circular arc created by all possible positions of a photon of a pair of coincident photons based on the energy produced by the photon by the processing device;
   calculating a second circular arc created by all possible positions of the photon based on the energy produced by the photon by the processing device;
   based on the energy produced, determining a scattering angle for each pair of coincident photons from an annihilation point relative to the position of the plurality of detectors by the processing device; and
   reconstructing an image using a reconstruction algorithm, wherein the reconstruction algorithm uses the scattering angle of each pair of coincident photons.

2. The method of claim 1, further comprising:
   identifying an annihilation area bounded by the first circular arc and the second circular arc; and
   identifying a plurality of possible locations of the annihilation point within the annihilation area.

3. The method of claim 2, further comprising:
   using the reconstruction algorithm to identify a plurality of possible locations of the annihilation point;
   matching the plurality of possible locations of the annihilation point within the annihilation area with the plurality of possible locations of the annihilation point identified from the reconstruction algorithm; and
   from the matching, determining an actual location of the annihilation point.

4. The method of claim 2, wherein the identifying a plurality of possible locations of the annihilation point within the annihilation area decreases a sensitivity of the positron emission tomography scan to the scattered photons.

5. The method of claim 1, further comprising:
   identifying an annihilation area bounded by a subject outline; and
   identifying the plurality of possible locations of the annihilation point within the annihilation area bounded by the subject outline.

6. The method of claim 1, wherein the measuring further comprises:
   constructing an outline of a subject;
   constructing one or more lines from a point of detection of one of the unscattered photons to each intersection of the outline of the subject with the first circular arc or the second circular arc;
   identifying an annihilation area bounded by three or more of the following: the one or more lines, the outline of the subject, and one of the first circular arc or the second circular arc; and identifying the plurality of possible locations of the annihilation point within the annihilation area.

7. The method of claim 1, wherein the reconstruction algorithm comprises a Maximum-Likelihood Expectation-Maximum algorithm.

8. The method of claim 1, wherein the reconstruction algorithm comprises an ordered subset expectation maximization algorithm.

9. The method of claim 1, wherein the reconstruction algorithm comprises a maximum a posteriori expectation maximization algorithm.

10. The method of claim 1, wherein the reconstruction algorithm comprises a filtered back projection algorithm.

11. The method of claim 1, wherein the reconstruction algorithm comprises a conjugate gradient algorithm.

12. The method of claim 1, wherein the reconstruction algorithm comprises a coincidence-list-ordered sets expectation-maximization algorithm.

13. A system for use in reconstructing an image from a positron emission tomography scan, wherein the system comprises:
   a processing device; and
   a non-transitory computer-readable storage medium in communication with the processing device,
   wherein the computer-readable storage medium contains one or more programming instructions that, when executed, cause the processing device to:
      detect a plurality of photons selected from scattered photons and unscattered photons;
      identify a time interval for each of the plurality of photons;
      match each of the plurality of photons into a plurality of pairs of coincident photons based upon a substantially simultaneous time interval identified;
      measure an energy produced by each of the plurality of photons;
      calculate a first circular arc created by all possible positions of a photon of a pair of coincident photons based on the energy produced by the photon;
      calculate a second circular arc created by all possible positions of the photon based on the energy produced by the second photon;
      identify an annihilation area bounded by the first circular arc and the second circular arc;
      identify a plurality of possible locations of the annihilation point within the annihilation area;
      based on the energy produced, determine a scattering angle for each pair of coincident photons from an annihilation point relative to a position of a plurality of detectors;
      measure an energy produced by a plurality of scattered photons from an annihilation event;
      match a plurality of pairs of coincident scattered photons based upon the energy measured;
      determine a scattering angle of each pair of coincident scattered photons from the plurality of pairs of coincident scattered photons; and
      reconstruct an image using a reconstruction algorithm, wherein the reconstruction algorithm uses the scattering angle of each pair of coincident scattered photons.

14. The system of claim 13, wherein the plurality of detectors further comprises a plurality of energy sensitive detectors.

15. The system of claim 14, wherein the computer-readable storage medium contains one or more programming instructions that, when executed, further causes the processing device to:
   direct the plurality of energy sensitive detectors to measure the energy produced by the plurality of scattered photons from the annihilation event.

16. The system of claim 13, wherein the computer-readable storage medium contains one or more programming instructions that, when executed, further causes the processing device to:
   use the reconstruction algorithm to identify a plurality of possible locations of the annihilation point;
   match the plurality of possible locations of the annihilation point within the annihilation area with the plurality of possible locations of the annihilation point identified from the reconstruction algorithm; and
   from the matching, determine an actual location of the annihilation point.

17. The system of claim 13, wherein the identifying a plurality of possible locations of the annihilation point within the annihilation area decreases a sensitivity of the positron emission tomography scan to the scattered photons.

18. The system of claim 13, wherein the reconstruction algorithm comprises a Maximum-Likelihood Expectation-Maximum algorithm.

19. The system of claim 13, wherein the reconstruction algorithm comprises an ordered subset expectation maximization algorithm.

20. The system of claim 13, wherein the reconstruction algorithm comprises a maximum a posteriori expectation maximization algorithm.

21. The system of claim 13, wherein the reconstruction algorithm comprises a filtered back projection algorithm.

22. The system of claim 13, wherein the reconstruction algorithm comprises a conjugate gradient algorithm.

23. The system of claim 13, wherein the reconstruction algorithm comprises a coincidence-list-ordered sets expectation-maximization algorithm.

24. A system of for use in reconstructing an image from a positron emission tomography scan, wherein the system comprises:
   a processing device; and
   a non-transitory computer-readable storage medium in communication with the processing device,
   wherein the computer-readable storage medium contains one or more programming instructions that, when executed, cause the processing device to:
      detect a plurality of photons selected from scattered photons and unscattered photons;
      identify a time interval for each of the plurality of photons;
      match each of the plurality of photons into a plurality of pairs of coincident photons based upon a substantially simultaneous time interval identified;
      measure an energy produced by each of the plurality of photons;
      identify an annihilation area bounded by a subject outline;
      identify a plurality of possible locations of the annihilation point within the annihilation area;
      based on the energy produced, determine a scattering angle for each pair of coincident photons from an annihilation point relative to a position of a plurality of detectors;
      measure an energy produced by a plurality of scattered photons from an annihilation event;
      match a plurality of pairs of coincident scattered photons based upon the energy measured;

determine a scattering angle of each pair of coincident scattered photons from the plurality of pairs of coincident scattered photons; and reconstruct an image using a reconstruction algorithm, wherein the reconstruction algorithm uses the scattering angle of each pair of coincident scattered photons.

25. The system of claim 13, wherein the computer-readable storage medium contains one or more programming instructions that, when executed, further causes the processing device to:

construct an outline of a subject;

construct one or more lines from a point of detection of one of the unscattered photons to each intersection of the outline of the subject with the first circular arc or the second circular arc;

identify the annihilation area bounded by the first circular arc, the second circular arc, and at least one of the one or more lines and the outline of the subject.

\* \* \* \* \*

UNITED STATES PATENT AND TRADEMARK OFFICE
CERTIFICATE OF CORRECTION

PATENT NO. : 8,866,087 B2
APPLICATION NO. : 13/977893
DATED : October 21, 2014
INVENTOR(S) : Pistorius et al.

It is certified that error appears in the above-identified patent and that said Letters Patent is hereby corrected as shown below:

In the Specification

Column 1, Lines 7-10, delete "The......................entirety." and insert -- The present application is a U.S. national stage filing under 35 U.S.C. §371 of International Application No. PCT/CA2012/050352, filed on May 29, 2012, the entire contents of which are incorporated herein by reference. --, therefor.

Column 4, Line 41, delete "(i.e," and insert -- (i.e., --, therefor.

Column 5, Line 30, delete "window $\Sigma$." and insert -- window $\tau$. --, therefor.

Column 7, Line 13, delete "$E_s$, is" and insert -- $E_s$ is --, therefor.

In the Claims

Column 18, Line 38, Claim 24, delete "system of for use" and insert -- system for use --, therefor.

Signed and Sealed this
Twenty-third Day of June, 2015

Michelle K. Lee
*Director of the United States Patent and Trademark Office*